(12) United States Patent
Nagasaki et al.

(10) Patent No.: US 9,327,034 B2
(45) Date of Patent: May 3, 2016

(54) BRANCHED POLYETHYLENE GLYCOL AND USE THEREOF

(71) Applicant: University of Tsukuba, Ibaraki (JP)

(72) Inventors: Yukio Nagasaki, Ibaraki (JP); Yutaka Ikeda, Ibaraki (JP); Hiromichi Kawasaki, Ibaraki (JP); Jinya Katamachi, Ibaraki (JP)

(73) Assignee: UNIVERSITY OF TSUKUBA, A JAPANESE NATIONAL UNIVERSITY, Ibaraki (JP)

( * ) Notice: Subject to any disclaimer, the term of this patent is extended or adjusted under 35 U.S.C. 154(b) by 35 days.

(21) Appl. No.: 14/363,884

(22) PCT Filed: Dec. 13, 2012

(86) PCT No.: PCT/JP2012/082333
§ 371 (c)(1),
(2) Date: Jun. 9, 2014

(87) PCT Pub. No.: WO2013/089182
PCT Pub. Date: Jun. 20, 2013

(65) Prior Publication Data
US 2014/0329290 A1    Nov. 6, 2014

(30) Foreign Application Priority Data

Dec. 14, 2011 (JP) ................................ 2011-273122
Jul. 12, 2012 (JP) ................................ 2012-156495

(51) Int. Cl.
| | |
|---|---|
| *A61K 8/72* | (2006.01) |
| *A61K 47/48* | (2006.01) |
| *C08G 65/32* | (2006.01) |
| *C07C 47/198* | (2006.01) |
| *C07D 211/40* | (2006.01) |
| *C08G 65/324* | (2006.01) |
| *C08G 65/333* | (2006.01) |
| *C08G 65/338* | (2006.01) |
| *A61K 8/86* | (2006.01) |
| *A61K 8/84* | (2006.01) |

(52) U.S. Cl.
CPC ......... *A61K 47/48215* (2013.01); *C07C 47/198* (2013.01); *C07D 211/40* (2013.01); *C08G 65/32* (2013.01); *C08G 65/324* (2013.01); *C08G 65/338* (2013.01); *C08G 65/33303* (2013.01); *A61K 8/72* (2013.01); *A61K 8/84* (2013.01); *A61K 8/86* (2013.01); *A61K 47/48* (2013.01); *A61K 47/48007* (2013.01); *A61K 47/48169* (2013.01); *A61K 47/48192* (2013.01); *C08G 2650/30* (2013.01); *C08L 2203/02* (2013.01)

(58) Field of Classification Search
None
See application file for complete search history.

(56) References Cited

FOREIGN PATENT DOCUMENTS

| | | |
|---|---|---|
| JP | 3-88822 | 4/1991 |
| JP | 11-322916 | 11/1999 |
| JP | 2005-520006 | 7/2005 |
| JP | 2005-538224 | 12/2005 |
| JP | 2007-527892 | 10/2007 |
| JP | 2011-084496 | 4/2011 |
| JP | 2011-521067 | 7/2011 |
| WO | 2010/033220 | 3/2010 |
| WO | 2010/059279 | 5/2010 |

OTHER PUBLICATIONS

International Preliminary Report on Patentability issued Jun. 17, 2014 in International (PCT) Application No. PCT/JP2012/082333.
Veronese et al., "A Branched Monomethoxypoly(ethylene glycol) for Protein Modification", Bioconjugate Chem., vol. 6, No. 1, 1995, pp. 62-69.
International Search Report issued Mar. 19, 2013 in International (PCT) Application No. PCT/JP2012/082333.
Extended European Search Report issued Nov. 19, 2015 in corresponding European Application No. 12857064.5.

*Primary Examiner* — James Rogers
(74) *Attorney, Agent, or Firm* — Wenderoth, Lind & Ponack, L.L.P.

(57) ABSTRACT

The present invention allows formation of covalent bonds in a bioactive compound having at least one amino group so as to efficiently provide the compound modified with PEG. The present invention thus provides a functionalized polyethylene glycol having a structure that allows reaction of two aldehyde groups with one amino group to form two covalent bonds.

10 Claims, 2 Drawing Sheets

LANE 1: MARKER
LANE 2: LYSOZYME
LANE 3: MONO-PEGYLATED LYSOZYME
        (DIALDEHYDE-TERMINATED PEG)

FIG. 3

FIG. 4

BRANCHED POLYETHYLENE GLYCOL AND USE THEREOF

TECHNICAL FIELD

The present invention relates to a novel branched polyethylene glycol and use thereof and more specifically to a functionalized biantennary polyethylene glycol and use thereof for improving biokinetics of amino group-containing drugs typically represented by bioactive proteins.

BACKGROUND ART

PEGylation of drug candidate proteins or nucleic acids have been useful for improving biokinetics thereof (in vivo retention, stability against proteases or nucleases, immunogenicity, etc). Numerous PEGylated proteins have been approved by FDA as medicines and many have been under development as well. Approved and commercialized medicines typically include PEG-asparaginase, PEG-adenosine deaminase, PEG-interferon α-2a, PEG-interferon α-2b, PEG-G-CSF, PEG-growth hormone receptor antagonists and nonproteinaceous medicines such as branched PEG-anti-VEGF aptamers. Among others, branched PEGs which become a branched form after binding to proteins have been recently attracting attention and contributing to development of new PEGylated medicines under recent difficult conditions to develop novel medicines (Non-Patent Document 1).

Most of branched PEGs used for PEGylated medicines so far are functionalized with active esters through which the PEGs can react with an amino group in proteins. However, the active esters generally react not only with lysine in proteins but also with histidine. Further during PEGylation in which PEGs having active ester terminal groups react with amino groups of proteins, the formation of an amide bond may significantly change the basicity (or the extent of positive charge) of the amino groups, resulting in significant decrease in protein activity. Thus there has been a need for establishment of the production technique of PEGylated proteins while maintaining the amino group basicity (or the extent of positive charge). The synthesis and purification of conventional branched PEGs is also disadvantageous in that it includes complex steps. Because of these problems of harsh reaction conditions, low reaction efficiency and generation of byproducts associated with the conventional PEGylation techniques, many proteins have not reached successful development in spite of expectation therefor as efficacious medicines.

PRIOR ART DOCUMENT

Non-Patent Document

Non-Patent Document 1: Bioconjugate Chem. 1995, 6, 62-69

SUMMARY OF THE INVENTION

Problem to be Solved by the Invention

Accordingly, an object of the present invention is to provide a compound for PEGylation or a PEGylation technique which allows reaction with, for example, a primary amine or a lysine residue or with an amino group of an N-terminal amino acid residue, when present, in a target protein upon PEGylation, allows no variation in the extent of positive charge of the amino group and can be produced by a simple manner compared to the production process of conventional compounds for branched PEGylation.

Means for Solving the Problem

The present inventors now have revealed for the first time that only an amino group can be selectively PEGylated according to the following scheme, for example.

Reaction scheme

[Chemical formula 1]

In the above formula, PEG is a polyethylene glycol chain and R is a residue or moiety of an amino compound other than an amino group.

Without wishing to be bound to any theory, it is understood that in the reaction scheme, the reaction between an amino group in a molecule to be modified and dialdehyde having two aldehyde groups (or formyl) in a modifying molecule allows formation of a ring structure, which allows efficient modification of the amino group. This modification method can proceed in a neutral aqueous solution and thus can be applied to various biomolecules. Only a primary amine (amino group) undergoes this reaction and a secondary amine (imino group) such as histidine does not undergo this reaction. The reaction proceeds efficiently under mild reaction conditions such as around neutral pH and allows alkylation of amino groups of proteins according to the binding manner that is completely different from the conventional PEGylation mechanism. Thus PEGylation by using the dialdehyde substance or a functionalized polyethylene glycol which is an analogue thereof capable of formation of the similar ring structure according to the above reaction scheme allows easy modification with polyethylene glycol of a compound having at least one reactive amino group, particularly a bioactive substance such as proteins, peptides, polynucleotides, oligonucleotides and other low molecular weight organic compounds in an aqueous solution at around neutral pH. Moreover, it has been found that the PEGylation of the present invention does not change the basicity (or the extent of positive charge) of the amino groups and thus can provide desired PEGylated compounds without significantly impairing the activity of bioactive substances to be modified.

Accordingly the present invention provides a functionalized polyethylene glycol represented by the following formula (I):

[Chemical formula 2]

(I)

where the moiety (hereinafter sometimes merely referred to as "A moiety")

[Chemical formula 3]

is selected from the group consisting of the following groups a to k:

[Chemical formula 4]

a b c d e f g h i j k each X independently represents —O—, —C(=O)O— or —C(=O)NH—;
each PEG independently represents —(CH$_2$CH$_2$—O—)$_q$R$^1$;
m and n are independently selected from integers of 1 to 12 respectively;
each R$^1$ independently represents a hydrogen atom or a C$_{1-6}$ alkyl; and
each q is independently selected from integers of 5 to 3000.

The functionalized polyethylene glycol, as described above, can react only with an amino group (—NH$_2$) in amine compounds or bioactive substances and thus has the reaction selectivity unlike polyethylene glycols having active ester terminal groups that may react with an amino group, an imino group as well as a hydroxyl group. In addition, the functionalized polyethylene glycol does not allow variation in the extent of positive charge of amino groups in the bioactive substances.

Thus other aspects of the present invention provide:
an agent for modification of an organic compound having at least one reactive amino group in the molecule, which includes the functionalized polyethylene glycol represented by the formula (I) as a reactant;
use of the functionalized polyethylene glycol represented by the formula (I) as a reactant for modification of an organic compound having at least one reactive amino group in the molecule; and
a method for producing a PEGylated bioactive substance comprising the step of reacting the functionalized polyethylene glycol represented by the formula (I) with a bioactive substance having at least one reactive amino group in the molecule under a condition at which two aldehyde groups of the functionalized polyethylene glycol can react with an amino group of the bioactive substance.

Advantageous Effects of the Invention

The functionalized polyethylene glycol represented by the formula (I) of the present invention allows modification (or PEGylation) of a bioactive substance having at least one reactive amino group in the molecule and thus can provide a product having significantly improved biokinetics (in vivo retention, resistance against in vivo metabolism, immunogenicity, etc.) compared to an unmodified bioactive substance while retaining at least a part of the activity of the unmodified substance.

DETAILED DISCLOSURE OF THE INVENTION

The present invention is more specifically described hereinafter.

In the context of the present invention, PEGylation means a modification by means of covalent binding of one or more polyethylene glycol (PEG) chains to a protein, a peptide or a non-peptide molecule.

The functionalized polyethylene glycol represented by the formula (I) is functionalized so that the reaction of two aldehyde groups (or formyl) in the molecule with an amino group in a compound having at least one reactive amino group such as a bioactive substance including proteins, peptides, polynucleotides, oligonucleotides and other low molecular weight organic compounds results in formation of an amine compound having a ring structure. The reactive amino group means an amino group that can react with two aldehyde groups of the functionalized polyethylene glycol and encompasses without limitation an amino group that can react so as to form a ring structure together with alkylene moieties to which the two aldehyde groups bind, regardless of the position of the amino group in the molecule of the bioactive substance. The molecule may contain one or more such amino groups.

In view of formation of a ring structure and particularly PEGylation of a compound having a plurality of amino groups such as a protein, the functionalized polyethylene glycol represented by the formula (I) preferably has the A moiety in the formula represented by the group a, b, c, d, e, for g, more preferably the group a, b, c or g and particularly preferably the group b or g.

The compound having at least one reactive amino group in the molecule may be free or immobilized or attached to a support (e.g., a carrier for in vivo implantation or a surface of a biosensor). The bioactive substance may be a medical, for example therapeutic or diagnostic protein, peptide, polynucleotide or oligonucleotide (siRNA, aptamer, etc.). "Protein" as used herein is a concept encompassing glycoproteins and lipoproteins which encompass natural proteins, recombinant proteins by means of gene engineering and fusion proteins. Thus, the amino group with which the functionalized polyethylene glycol of the formula (I) reacts may be in a sugar residue in a glycoprotein.

The bioactive substance is preferably a medical, e.g., therapeutic or diagnostic protein or peptide and may include enzymes (e.g., asparaginase, adenosine deaminase, etc.), cytokines (e.g., interleukin 1, 2, 6, etc., interferon α, β or γ, tumor necrosis factors, lymphotoxins, colony-stimulating factors, erythropoietin, epidermal growth factor, fibroblast growth factors, etc.), soluble receptor proteins (e.g., derived from tumor necrosis factor receptors, receptors for various interleukins, tyrosine kinase receptors, etc.), hormones (e.g., insulin, human growth hormones, etc.), antibodies (e.g., anticancer, anti-allergy and anti-infectious disease antibodies) and active fragments thereof.

In the groups a to k as the A moiety in the formula (I), m and n are independently selected from integers of 1 to 12, preferably 1 to 6. Each PEG independently represents —(CH$_2$CH$_2$—O—)$_q$R$^1$, wherein R$^1$ represents a hydrogen atom or a C$_{1-6}$ alkyl, of which alkyl group may be linear or branched and may include, but not limited to, methyl, ethyl, n-propyl, iso-propyl, n-butyl, iso-butyl, t-butyl, n-pentyl and n-hexyl among which methyl or ethyl is preferred. Each q may not be limited and may be any integer as far as the object of the present invention can be achieved, and may be 5 to 3000, preferably 8 to 1000, more preferably 12 to 700 and particularly preferably 20 to 600. Each X in the A moiety may independently be —O—, —C(=O)O— or —C(=O)NH—, among which —O— is preferable in view of binding stability and the like.

It is understood that a person skilled in the art can easily provide the functionalized polyethylene glycol of the present invention by referring to the structure represented by the formula (I) and utilizing well known starting materials or well known methods in the art. Conveniently, the functionalized polyethylene glycol of the present invention is effectively produced according to the following reaction scheme.

[Chemical formula 5]

In the above formula, the A moiety is as defined for the formula (I) except that X is —O— and R$^1$ is a methyl group; the A$^1$ moiety is selected from the following groups a' to k'; the A$^2$ moiety has the same meaning as the A moiety except that R$^1$ is H.

[Chemical formula 6]

scheme, the functionalized polyethylene glycol of the formula (I) can be efficiently produced. The thus provided functionalized polyethylene glycol can be referred to as a so-called monodisperse polymer having Mw/Mn of 1.07 or less, preferably 1.05 or less.

The functionalized polyethylene glycol of the formula (I) allows branched PEGylation of the bioactive substance having an amino group as described above by reaction thereof with the free compound having an amino group in the molecule or the compound having an amino group in the molecule immobilized on the surface of a material or on a material chip in a reaction solvent such as water, methanol, ethanol or tetrahydrofuran (THF) which may be buffered as required at a temperature from cooling temperature (e.g., 4° C.) to 100° C., preferably 4 to 37° C. until completion of the reaction.

Thus the condition at which two aldehyde groups of the functionalized polyethylene glycol can react with an amino group of the bioactive substance as referred to in the production method of the present invention consists preferably in stirring the reaction mixture at 4 to 37° C. for 4 to 72 hours. Accordingly the bioactive substance, for example, a protein or a peptide can be effectively modified with the branched polyethylene glycol.

The above starting material having the $A^1$ moiety is well known per se or is well known as described in Japanese Translation of PCT Application No. 2011-84496 which discloses a part of inventions by the present inventors or can be produced by a production method that is a modification of the production methods of the well known compounds. Typical starting materials may include the compounds represented by the following structure formulae.

[Chemical formula 7]

Each reaction in the above reaction scheme per se is well known and can be carried out according to the steps described in the following Examples or with modifications thereto, if necessary. For example, the first step corresponds to ring opening anionic polymerization, preferably living anionic polymerization, of an ethylene oxide. The second step is etherification (or alkylation) of a hydroxyl group at a terminal of polyethylene glycol and can be carried out by a well known synthesis method per se. The third step is oxidative hydroxylation of an unsaturated double bond and the fourth step is a step of Malaprade oxidation of two vicinal hydroxyl groups, which are all thoroughly studied and are well known reactions in the art. Thus according to these steps in the reaction f g h i j k

In the formulae, n and m have the same meanings as defined in the formula (I).

Alternatively, the starting material having the above $A^1$ moiety can provide the functionalized polyethylene glycol of the formula (I) wherein X is independently represented by —C(=O)O— or —C(=O)NH— by oxidizing the —CH$_2$OH moieties respectively in —(CH$_2$)$_m$—OH and —(CH$_2$)$_n$—OH to convert to —COOH which is then subjected to reaction with HO-PEG or H$_2$N-PEG.

BEST MODE FOR CARRYING OUT THE INVENTION

The present invention is hereinafter more specifically described by way of specific examples which do not limit the present invention. According to the present invention, bioactive proteins were efficiently PEGylated while constantly retaining the activity of the proteins.

EXAMPLES

In order to describe the present invention in a simple manner, examples of the compounds of the formula (I) wherein the A moiety is the groups (b) and (g), X is —O— and m and n are respectively an integer of 1 are described hereinbelow. However, it is not intended that the present invention is limited to these examples.

Example 1

Production of Functionalized Polyethylene Glycol (PEG) (which Followed the Synthesis Scheme Shown Below)

[Chemical formula 8]

(1) Synthesis of Compound 2

The instruments used in the present synthesis were preliminarily dried in a drying chamber at 120° C. for 10 hours. To a 200-mL pear-shaped evaporating flask was added the compound 1 (64 mg, 0.50 mmol) to which flask a three-way stopcock was equipped. While purging with nitrogen gas, a distilled THF solvent (30 mL) and potassium naphthalene (0.30 M, 3.37 mL, 1.00 mmol) were added prior to stirring for 15 minutes. Ethylene oxide (5.58 mL, 0.11 mol) was further added and the mixture was stirred at 25° C. for 60 hours. After the reaction, reprecipitation was carried out with 1.50 L of freezer-chilled 2-propanol (IPA). The supernatant was removed by centrifugation to isolate the reaction product. The reaction product was dissolved in methanol, recovered in a 200-mL pear-shaped evaporating flask, concentrated on an evaporator and reprecipitated again. Reprecipitation was repeated 3 times. After the third evaporation, the reaction product was dissolved in 10 mL of 1,4-dioxane and freeze-dried. After freeze-drying, the compound 2 was obtained with the yield of 93%.

$^1$H NMR (CDCl$_3$, 400 MHz)

5.53 ppm (s, 2H), 3.83-3.45 ppm (m, 976H), 3.36 ppm (s, 4H), 2.76 ppm (br, 2H), 2.18 ppm (s, 4H)

GPC Mn 9459, Mw/Mn 1.19

(2) Synthesis of Compound 3

To a 100-mL pear-shaped evaporating flask was added the compound 2 (920 mg, 0.10 mmol) to which flask a three-way stopcock was equipped. A THF solvent (15 mL) was added to the flask which was then immersed in an ice bath at 0° C. while NaH (24.0 mg, 0.60 mmol) was added and stirred for 30 minutes. CH$_3$I (0.5 mL, 8.0 mmol) was then added and the mixture was stirred at room temperature for 30 hours. After the reaction, NaH was removed by filtration through Celite and the reaction product was concentrated on an evaporator. Reprecipitation was carried out with 200 mL of freezer-chilled 2-propanol (IPA). After centrifugation, the reaction product was separated from the solvent which was discarded. The reaction product was dissolved in methanol, recovered in a 200-mL pear-shaped evaporating flask and concentrated on an evaporator. Reprecipitation was repeated 3 times. After the third evaporation, the reaction product was dissolved in 5 mL of 1,4-dioxane and freeze-dried. After freeze-drying, the compound 3 was obtained with the yield of 85%.

$^1$H NMR (CDCl$_3$, 400 MHz)

5.54 ppm (s, 2H), 3.83-3.45 ppm (m, 976H), 3.38 ppm (s, 6H), 3.36 (s, 4H), 2.18 (s, 4H)

GPC Mn 10015, Mw/Mn 1.13

(3) Synthesis of Compound 4

In a 100-mL vial, the compound 3 (500 mg, 0.01 mmol) was dissolved in acetone (3 mL), water (3 mL) and acetonitrile (3.0 mL) and N-methylmorpholine N-oxide (60.0 mg, 0.5 mmol) and microcapsulated osmium tetroxide (10.1 mg) were added. The mixture was shaken at room temperature for 48 hours. After the reaction, osmium tetroxide was removed by filtration and the reaction product was concentrated by evaporation. Reprecipitation was then carried out with 200 mL of freezer-chilled 2-propanol (IPA). The supernatant was removed by centrifugation to isolate the reaction product. The reaction product was dissolved in methanol, recovered in a 200-mL pear-shaped evaporating flask, concentrated on an evaporator and reprecipitated again. Reprecipitation was repeated 3 times. After the third evaporation, the reaction product was dissolved in 5 mL of 1,4-dioxane and freeze-dried. After freeze-drying, the compound 4 was obtained with the yield of 91%.

$^1$H NMR (CDCl$_3$, 400 MHz)

3.92-3.90 ppm (br, 2H), 3.83-3.45 ppm (m, 976H), 3.38 ppm (s, 6H), 3.35 ppm (s, 2H), 3.26-3.28 (m, 2H), 3.21 ppm (s, 2H), 1.85-1.65 (m, 4H)

GPC Mn 9319, Mw/Mn 1.14

(4) Synthesis of Compound 5

Sodium periodate (2.70 mg, 0.013 mmol) was dissolved in water (500 µL) and the compound 4 (101 mg, 0.01 mmol) was added dropwise to the solution prior to stirring at room temperature for 1 hour. After the reaction, extraction with dichloromethane, dehydration over sodium sulphate and concentration of the reaction product on an evaporator were carried out. The reaction product was dissolved in 5 mL of 1,4-dioxane and freeze-dried. After freeze-drying, the compound 5 was obtained with the yield of 15%.

$^1$H NMR (CDCl$_3$, 400 MHz)

9.79-9.78 ppm (t, 2H), 3.83-3.45 ppm (m, 976H), 3.51 ppm (s, 4H), 3.38 (s, 6H), 2.57 (d, 4H)

GPC Mn 10325, Mw/Mn 1.23

Example 2

Synthesis of Branched PEGylated Protein Using Compound 5

The synthesized branched PEG (compound 5, 10 kDa) was added to chicken lysozyme (molecular weight: about 14.3 kDa) at a 5-fold equivalent and reaction therebetween was carried out in a 0.1-M sodium phosphate buffer (pH 7.0) at 4° C. for 6 hours.

Figure 1:
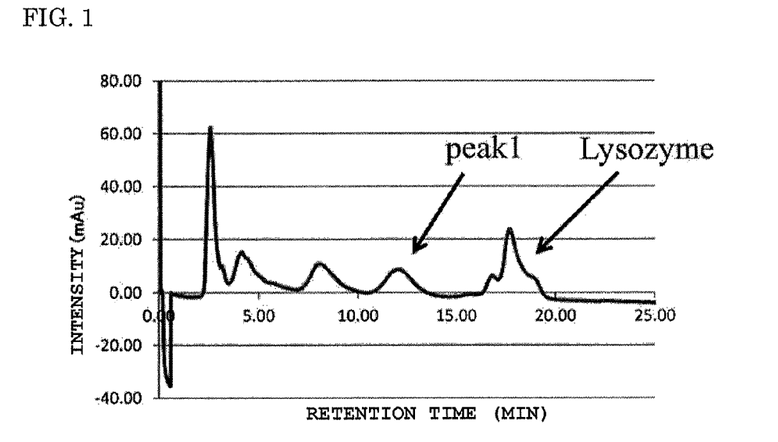
FIG. 1 is a HPLC chart illustrating the HPLC analysis result of a reaction product obtained by PEGylation of lysozyme with the functionalized polyethylene glycol of the present invention in Example 2 described hereinbelow, and "peak 1" in the figure corresponds to the peak 1 of the fraction containing the reaction product and "Lysozyme" corresponds to the peak of the fraction containing lysozyme prior to PEGylation.

The HPLC chart representing the result of HPLC (high performance liquid chromatography) of lysozyme and the reaction product is shown in FIG. 1.

Figure 2:
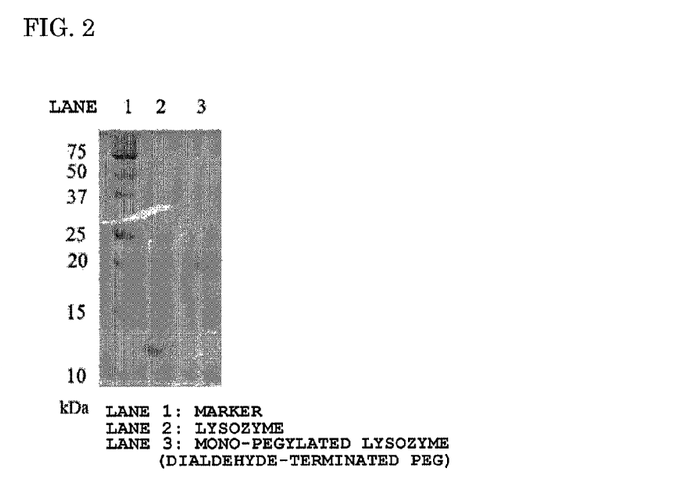
FIG. 2 is a photographic image substituting a drawing representing the SDS-PAGE analysis results of the fraction of the peak 1 in FIG. 1, lysozyme and a molecular weight marker, and Lanes 1, 2 and 3 respectively represent the migration results of the marker, lysozyme and the fraction of the peak 1 (PEGylated lysozyme).

The peak 1 obtained from HPLC was isolated and analyzed on SDS-PAGE of which result is shown in FIG. 2.

The above analyses results and the results from the model synthesis described hereinbelow showed that the peak 1 corresponds to a PEGylated lysozyme having a molecular weight that is about 10 kDa higher than that of lysozyme and having one branched PEG bound to lysozyme.

Example 3

Production of Functionalized Polyethylene Glycol (PEG) (which Followed the Synthesis Scheme Below)

[Chemical formula 9]

(1) Synthesis of Compound 2

The instruments used in the present synthesis were preliminarily dried in a drying chamber at 120° C. for 10 hours. To a 100-mL pear-shaped evaporating flask was added the compound 1 (0.07 g, 0.50 mmol) to which flask a three-way stopcock was equipped. While purging with nitrogen gas, a distilled THF solvent (30 mL) and potassium naphthalene (0.30 M, 3.37 mL, 1.00 mmol) were added prior to stirring for 15 minutes. Distilled ethylene oxide (5.60 mL, 0.11 mol) was further added and the mixture was stirred for 60 hours. After the reaction, reprecipitation was carried out with 1.50 L of freezer-chilled IPA. The supernatant was removed by centrifugation to isolate the reaction product. The reaction product was dissolved in methanol, recovered in a 200-mL pear-shaped evaporating flask, concentrated on an evaporator and reprecipitated again. Reprecipitation was repeated 3 times. After the third evaporation, the reaction product was dissolved in 5 mL of 1,4-dioxane and freeze-dried. After freeze-drying, the compound 2 was obtained with the yield of 86%.

GPC Mn 7815, Mw/Mn=1.05

(2) Synthesis of Compound 3

To a 200-mL pear-shaped evaporating flask was added the compound 2 (723 mg, 0.10 mmol) to which flask a three-way stopcock was equipped. A THF solvent (15 mL) was added to the flask which was then immersed in an ice bath at 0° C. while sodium hydride (58.8 mg, 1.47 mmol) was added and stirred for 30 minutes. Methyl iodide (0.75 mL, 12.0 mmol) was then added and the mixture was stirred at room temperature for 48 hours. After the reaction, insoluble matters were removed by filtration through Celite and the reaction product was concentrated on an evaporator. Reprecipitation was carried out with freezer-chilled IPA (1.5 L). After centrifugation, the reaction product was separated from the solvent which was discarded. The reaction product was dissolved in methanol, recovered in a 200-mL pear-shaped evaporating flask and concentrated on an evaporator. Reprecipitation was repeated 3 times. After the third evaporation, the reaction product was dissolved in 5 mL of 1,4-dioxane and freeze-dried. After freeze-drying, the compound 3 was obtained with the yield of 73%.

GPC Mn 7803, Mw/Mn=1.05

(3) Synthesis of Compound 4

In a 100-mL vial, the compound 3 (434 mg, 0.06 mmol) was dissolved in acetone (3.0 mL), water (3.0 mL) and acetonitrile (3.0 mL) and N-methylmorpholine N-oxide (57.3 mg, 0.49 mmol) and osmium tetroxide (12.5 mg, 0.05 mmol) were added. The mixture was shaken at room temperature for 48 hours. After the reaction, osmium tetroxide was removed by filtration and the reaction product was concentrated by evaporation. Reprecipitation was then carried out with freezer-chilled IPA (200 mL). The supernatant was removed by centrifugation to isolate the reaction product. The reaction product was dissolved in methanol, recovered in a 200-mL pear-shaped evaporating flask, concentrated on an evaporator and reprecipitated again. Reprecipitation was repeated 3 times. After the third evaporation, the reaction product was dissolved in 5 mL of 1,4-dioxane and freeze-dried. After freeze-drying, the compound 4 was obtained with the yield of 87%.

GPC Mn 7869, Mw/Mn=1.04

(4) Synthesis of Compound 5

Sodium periodate (5.23 mg, 0.02 mmol) was dissolved in a mixture of water (100 μL) and methanol (400 μL) to which the compound 4 (147 mg, 0.02 mmol) was added dropwise and stirred for 1 hour. After the reaction, extraction with dichloromethane, dehydration over sodium sulphate and concentration of the reaction product on an evaporator were carried out. The reaction product was dissolved in 5 mL of 1,4-dioxane and freeze-dried. After freeze-drying, the compound 5 was obtained with the yield of 45%.

GPC Mn 7849, Mw/Mn=1.05

Example 4

Synthesis of Branched PEGylated Protein Using Compound 5

Lysozyme (1.5 mg) was dissolved in 150 μL of a carbonate buffer at pH 10.35 (0.05 mM). The solution (70 μL) was added to an eppendorf tube containing 4.0 mg (5-fold equivalent to lysozyme) of the compound 5, 600 μL of the carbonate buffer at pH 10.35 (0.05 mM) was further added and the mixture was left to stand so that the reaction proceeded at room temperature for 36 hours. The solution after the reaction was analyzed on HPLC and the peak of the PEGylated lysozyme was recovered and purified on a desalting column.

Figure 4:
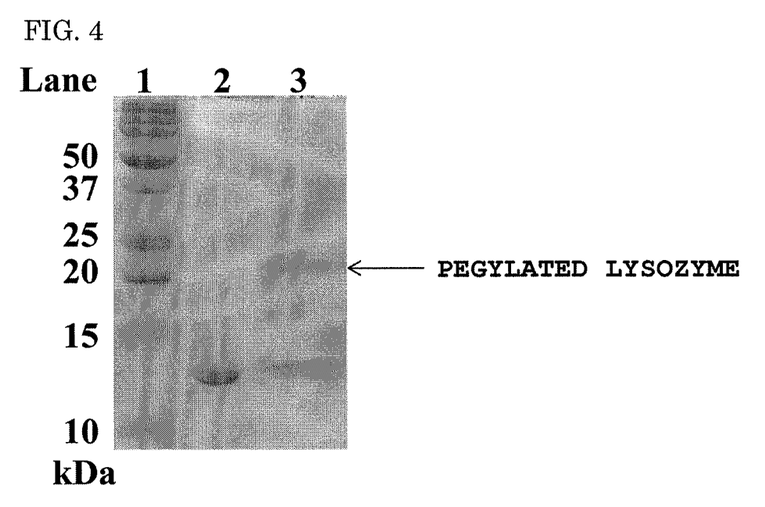
FIG. 4 is a photographic image substituting a drawing representing the SDS-PAGE analysis results of the reaction product (Lane 3) obtained by PEGylation of lysozyme with the functionalized polyethylene glycol of the present invention in Example 4 described hereinbelow, and Lanes 1, 2 and 3 respectively represent the migration results of a protein marker, lysozyme and the PEGylated lysozyme fraction.

The SDS-PAGE analysis result of the recovered fraction containing the PEGylated lysozyme by HPLC is shown in FIG. 4.

Example 5

Model Synthesis

In order to analyze the structure at the binding site of the synthesized branched PEG compounds and amino groups, the branched PEGs (about 5 kDa) synthesized by the same manner as the above compounds 5 were reacted with 2-aminoethanol to carry out the structure analysis. The results by MALDI-TOF MS revealed that the amino groups and the branched PEGs are bound as shown in the reaction scheme below.

[Chemical formula 10]

Calculated (n+m=98): 4567.408 [M+H]$^+$
Measured: 4569.961 [M+H]$^+$

Test Example 1

Evaluation of Activity of PEGylated Lysozyme

This test example is to evaluate the relative residual activity, relative to the activity of non-PEGylated lysozyme, of the branched PEGylated (10 kDa) lysozyme obtained by the manner as described in Example 2 (example of the present invention) and a single chain PEGylated (5 kDa) lysozyme (control) obtained by adding conventional N-hydroxysuccinimide activated ester PEG (NOF Corporation: ME-050HS; Comparative Example) to chicken lysozyme (molecular weight: about 14.3 kDa) at a 5-fold equivalent to allow synthesis reaction therebetween in a 0.1-M sodium phosphate buffer (pH 7.0) at 4° C. for 3 hours followed by isolation and purification.

Figure 3:
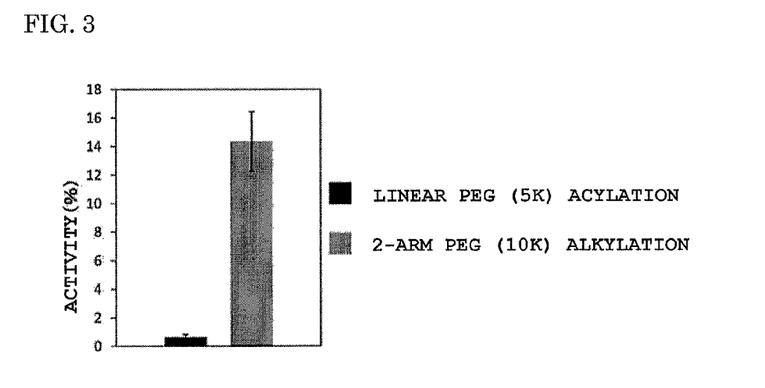
FIG. 3 is a graph illustrating relative residual activity, relative to the activity of unmodified lysozyme, of PEGylated lysozymes obtained by PEGylation of lysozyme with the functionalized polyethylene glycol according to the present invention and with a conventional active ester-type polyethylene glycol.

The test was carried out with a substrate Micrococcus lysodeikticus. To 800 μL of a 66-mM sodium phosphate buffer (pH 6.2) containing 0.24 mg of the substrate was added 200 μL of a 66-mM sodium phosphate buffer (pH 6.2) containing the PEGylated lysozyme (0.8 μg) and bovine serum albumin (20 μg) and the mixture was measured for an absorbance at 450 nm for 5 minutes to determine the activity for hydrolysis of the substrate. The results are shown in the graph in FIG. 3. FIG. 3 reveals that the control PEGylated lysozyme which contains only one linear PEG significantly lost the activity thereof resulting in about 1% of the intrinsic activity, while the PEGylated lysozyme obtained by PEGylation with the branched PEG according to the present invention retained significantly high lysozyme activity.

INDUSTRIAL APPLICABILITY

According to the present invention, the functionalized polyethylene glycol can be provided which allows efficient modification of various bioactive compounds having an amino group with the branched polyethylene glycol without varying the extent of positive charge of the amino group. Thus the present invention can be used in, but not limited to, drug manufacturing industry.

The invention claimed is:

1. A functionalized polyethylene glycol selected from the group consisting of groups a to k:

-continued wherein each X represents —O—, —C(=O)O— or —C(=O)NH—;
m and n are independently selected from integers of 1 to 12 respectively;
each PEG independently represents —(CH$_2$CH$_2$—O—)$_q$R$^1$;
each R$^1$ independently represents a hydrogen atom or a C$_{1-6}$ alkyl; and
respective q is independently selected from integers of 5 to 3000.

2. The functionalized polyethylene glycol according to claim 1 selected from the group consisting of the groups a, b, c, d, f and g.

3. The functionalized polyethylene glycol according to claim 1 selected from the group consisting of the groups a, b, c, d, f and g, wherein X is —O—.

4. The functionalized polyethylene glycol according to claim 1 selected from the group consisting of groups b and g, wherein each X is —O—, and
each q is independently 8 to 1000.

5. A PEGylated bioactive substance produced by reacting the functionalized polyethylene glycol according to claim 1 with a bioactive substance having in a molecule at least one reactive amino group.

6. A method for modification of an organic compound having at least one reactive amino group in the molecule, comprising reacting the organic compound with the functionalized polyethylene glycol according to claim 1.

7. A method for producing a PEGylated bioactive substance comprising a step of reacting the functionalized polyethylene glycol according to claim 1 with a bioactive substance having at least one reactive amino group under a condition at which two aldehyde groups of the functionalized polyethylene glycol can react with an amino group of the bioactive substance.

8. The PEGylated bioactive substance according to claim 5, wherein the bioactive substance is a therapeutic protein.

9. The method according to claim 7, wherein the bioactive substance is a therapeutic protein.

10. The PEGylated bioactive substance according to claim 8, wherein the therapeutic protein is selected from the group consisting of an enzyme, a cytokine, a soluble receptor protein, an antibody and an antibody fragment.

* * * * *